(12) United States Patent
Huang et al.

(10) Patent No.: US 11,299,789 B2
(45) Date of Patent: Apr. 12, 2022

(54) LOOP-MEDIATED ISOTHERMAL AMPLIFICATION (LAMP) BASED ASSAY FOR DETECTING MICROBES

(71) Applicant: California Institute of Technology, Pasadena, CA (US)

(72) Inventors: Xiao Huang, Pasadena, CA (US); Michael R. Hoffmann, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 421 days.

(21) Appl. No.: 16/237,458

(22) Filed: Dec. 31, 2018

(65) Prior Publication Data

US 2019/0203268 A1 Jul. 4, 2019

Related U.S. Application Data

(60) Provisional application No. 62/612,978, filed on Jan. 2, 2018.

(51) Int. Cl.
| | | |
|---|---|---|
| *C12P 19/34* | (2006.01) | |
| *C12Q 1/689* | (2018.01) | |
| *G02B 21/34* | (2006.01) | |
| *G02B 21/16* | (2006.01) | |
| *C12Q 1/70* | (2006.01) | |
| *C12Q 1/6844* | (2018.01) | |

(52) U.S. Cl.
CPC .......... *C12Q 1/689* (2013.01); *C12Q 1/6844* (2013.01); *C12Q 1/70* (2013.01); *G02B 21/16* (2013.01); *G02B 21/34* (2013.01)

(58) Field of Classification Search
CPC .................................................. C12Q 1/6853
See application file for complete search history.

(56) References Cited

U.S. PATENT DOCUMENTS

2009/0105082 A1* 4/2009 Chetverin ............... C12Q 1/68
506/7
2014/0220667 A1 8/2014 Ahmed
2016/0319354 A1 11/2016 Tocigl et al.
2017/0159136 A1* 6/2017 Church ................ C07H 21/04
2018/0037944 A1 2/2018 Roy et al.

FOREIGN PATENT DOCUMENTS

WO 2017/116220 A1 7/2017

OTHER PUBLICATIONS

Lam et al., Biomed Microdevices 10, 539-546 (2008). (Year: 2008).*
Esmatabadi et al., "Techniques for Evaluation of LAMP Amplicons and their Applications in Molecular Biology", Asian Pacific Journal of Cancer Prevention, Dec. 2015, vol. 16, pp. 7409-7414.
Mori et al., "Sequence specific visual detection of LAMP reactions by addition of cationic polymers", BMC Biotechnology, Jan. 10, 2006, vol. 6, pp. 1-10.
Tilli et al., "Bacteria Screening, Viability, and Confirmation Assays Using Bacteriophage-Impedimetric/Loop-Mediated Isothermal Amplification Dual-Response Biosensors", Analytic Chemistry, Mar. 20, 2013, vol. 85, pp. 4893-4901.
Young, Lee W., International Search Report and Written Opinion, United States Patent and Trademark Office, PCT/US2018/068216, dated Mar. 28, 2019.
Wittmann-Regis, Agnes, International Preliminary Report on Patentability and Written Opinion, The International Bureau of WIPO, PCT/US2018/068216, dated Jul. 16, 2020.

* cited by examiner

*Primary Examiner* — Kenneth R Horlick
(74) *Attorney, Agent, or Firm* — Gavrilovich, Dodd & Lindsey LLP

(57) ABSTRACT

A method and system are disclosed for detecting microbial pathogens in a sample suspected of containing the pathogens. The method includes combining loop-mediated isothermal amplification (LAMP) reagents and a polymer gel, such as a hydrogel, together with the sample to form a mixture. The gel polymerizes over a short time to immobilize the viral particles within the mixture. If target DNA/RNA are present in the sample, amplicons are produced. The target microorganisms are detected by visually detecting the presence or absence of the amplicons. The target microorganism concentrations may be determined based on the number of fluorescent amplicon dots after the reaction using a smartphone or a fluorescent microscope. The method may be employed for rapidly and inexpensively quantifying microbial pathogens in environmental water samples with high sensitivity.

2 Claims, 5 Drawing Sheets

Specification includes a Sequence Listing.

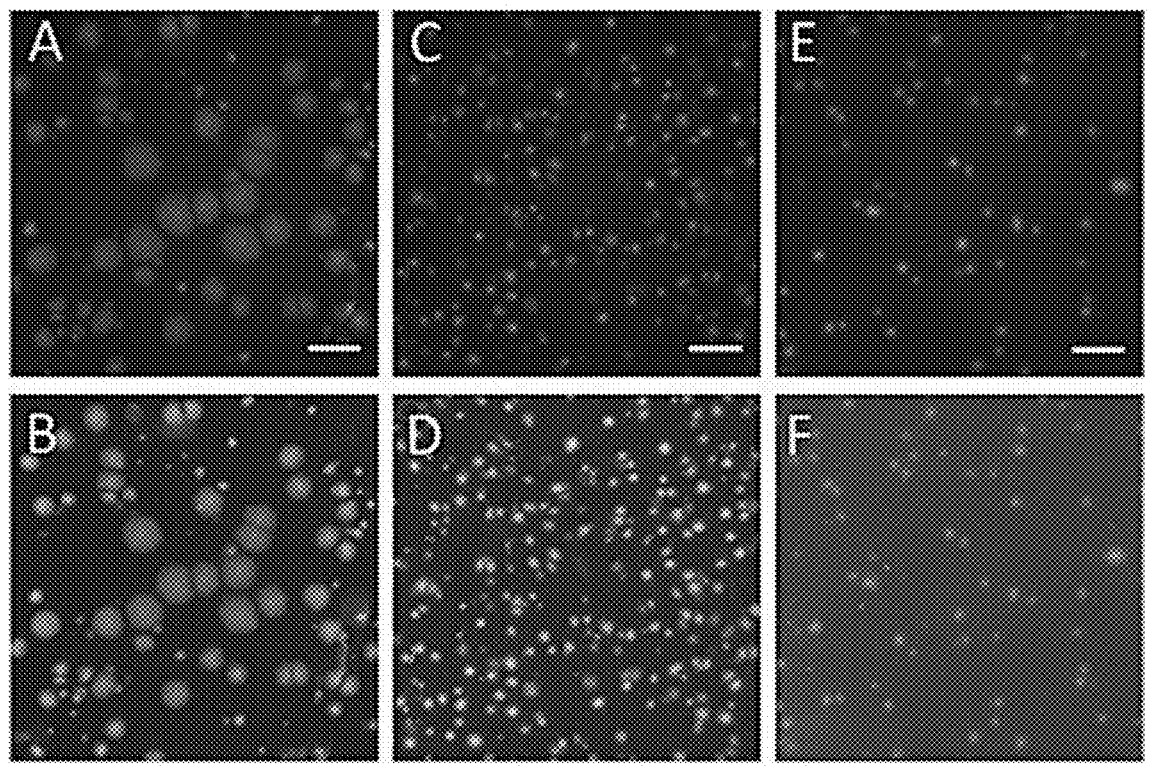
Figure 3A-F
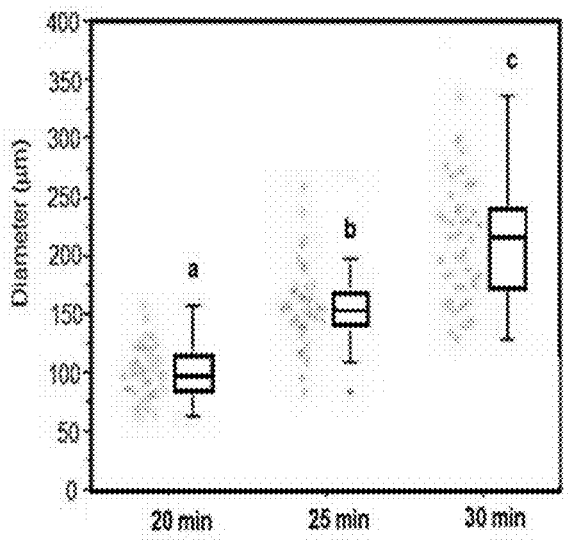
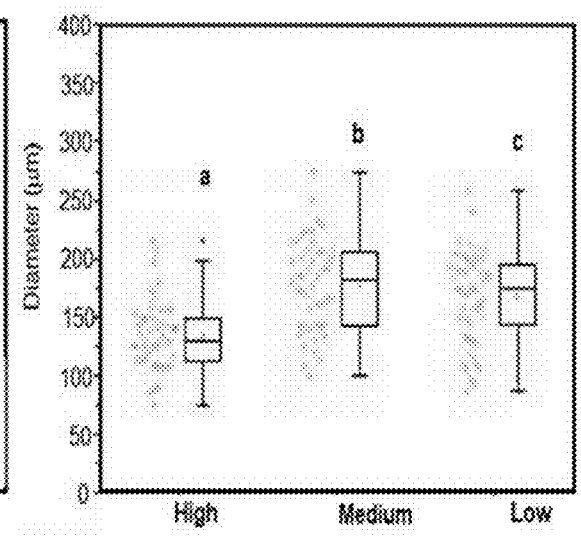
Figure 4A
Figure 4B

| Primer Name | Genome position | Sequence (5'-3') | Source |
|---|---|---|---|
| F3 | 2520-2539 | CTTGCGACGATAGACTTATC | |
| B3 | 2776-2759 | TAGATGCCTATGGTTCCG | |
| FIP (F1c + F2) | 2658-2638(F1c) + | ATCGTATCGTCTCGCCATCTA + | |
| | 2586-2607(F2) | CCACCAGAGCTATATTCATATC | 1 |
| BIP (B1c + B2) | 2673-2693(B1c) + | ACAATGGGAAATGGGTTCACA + | |
| | 2739-2722(B2) | GGGTCGCTTTGACTATTG | |
| LF | 2636-2619 | GATTCCGTAGTGTGAGCG | |
| LB | 2699-2720 | GCTAGAGTCCATGATATTCTGG | |
| 5'FAM-FIP | 2658-2638(F1c) + | FAM-ATCGTATCGTCTCGCCATCTA + | |
| | 2586-2607(F2) | CCACCAGAGCTATATTCATATC | 1 |
| qFIP-3'IBFQ | | GAGACGATACGAT-IBFQ | |

Figure 7

LOOP-MEDIATED ISOTHERMAL AMPLIFICATION (LAMP) BASED ASSAY FOR DETECTING MICROBES

CROSS REFERENCE TO RELATED APPLICATIONS

This Application claims the benefit of U.S. Provisional Patent Application Ser. No. 62/612,978, filed on Jan. 2, 2018, which is incorporated by reference herein in its entirety.

TECHNICAL FIELD

The present disclosure generally relates to techniques for detecting microbes of interest in an environmental sample, and more particularly, to detection techniques based on loop-mediated isothermal amplification (LAMP).

BACKGROUND

Waterborne diseases are illness caused by pathogenic microorganisms (e.g., viruses, bacteria and protozoa). According to the World Health Organization (WHO), waterborne diarrheal diseases alone are responsible for the deaths of 1.8 million people every year, which makes it the leading cause of disease and death around the world. The detection of microbial pathogens in environmental waters is challenging due to their small sizes and large diversities.

Currently, a variety of methods are available for waterborne microbial pathogen detection. These methods can be divided into two categories. The first category is traditional culture-based methods, which is based upon providing a combination of nutritional and physicochemical conditions that will support the growth of the microorganisms of interest. Yet providing a similar environment like the pathogens' warm-blooded hosts could be difficult or in some cases, not possible. Additionally, culture-based methods are usually time (days to weeks) and labor consuming, and therefore, can only be carried out in well-equipped laboratories by trained technicians. Another category is molecular-based methods, such as polymerase chain reaction (PCR), immunoassays, and various biosensors. PCR, especially the quantitative PCR (qPCR) method, is the most widely used pathogen detection method, and has been considered as the new gold standard test. qPCR provide a much shorter sample-to-result time (3 to 5 hours). However, despite its wide acceptance, qPCR is limited by the reliance on standard reference materials (standard curve) for quantification. Unreliable and inconsistent commercial standard reference materials may also affect the accuracy of qPCR quantification. Also, qPCR is prone to inhibition caused by substances naturally present in environmental samples (e.g., heavy metals and organic matter), thereby leading to inaccurate target quantification or false-negative results.

Compared to qPCR, recent digital PCR techniques have been shown to be a more robust solution for microbial pathogen detection in environmental samples. Digital PCR is based on partitioning and Poisson statistics, as such, no comparative external quantitative standards are needed to quantify samples of unknown concentrations. However, the implementation of digital PCR methods to point-of-use applications can be challenging. This is because digital PCR requires costly instruments (i.e., the Bio-rad droplet digital PCR), a well-equipped laboratory environment, and trained personnel to perform the assay. These factors severely restrict accessibility and adoption of digital PCR in resource-limited settings.

Accordingly, a rapid, simplified, low-cost assay for detecting microbes is desirable to deliver the benefits of molecular assays beyond centralized laboratories, for example, in situations requiring point-of-use field testing of environmental waters in places with limited resources.

SUMMARY

Alternative to PCR-based nucleic acid amplification and detection techniques, isothermal amplification methods, such as loop mediated isothermal amplification (LAMP), helicase-dependent amplification (HDA), multiple displacement amplification (MDA), and rolling circle amplification (RCA), offer the opportunity to deliver the benefits of molecular assays beyond centralized laboratories. With no need for thermal cycling, isothermal reactions are more suitable to be coupled with miniaturized, portable, and battery-powered "lab-on-a-chip" platforms. Initially described in 2000, LAMP has become the most popular isothermal amplification technique covering almost all sanitation important microbial pathogens. LAMP is capable of amplifying a target DNA template $10^9$ times in less than 30 min at a temperature around 65° C. Additionally, LAMP products can be detected by fluorescence using intercalating dyes (e.g., EvaGreen, Sybr Green, and SYTO9) or with unaided eyes through turbidity changes caused by magnesium pyrophosphate precipitation as a byproduct of amplification.

Portable devices have been developed to facilitate the application of LAMP in point-of-care disease diagnostics. However, most of these assays are qualitative, and thus not suitable for quantitative environmental water quality monitoring. Although several quantitative LAMP assays have been reported in the real-time or digital formats, these assays all require complex instrumentation (i.e., handheld real-time fluorescence detection devices) or custom microfabricated consumables (e.g., Slipchip and DropChip).

Disclosed herein are LAMP-based techniques and systems that can provide quantitative, low-cost, and rapid bacteriophage detection and/or monitoring tool, which can be easily adopted in resource-limited settings. Inspired by earlier work on in situ PCR, immobilization of microbes in hydrogels, PCR amplification in polyacrylamide gels, and MDA amplification in polyethylene glycol (PEG) hydrogels, a novel in-gel LAMP (gLAMP) technique is described herein that is capable of quantifying microbial pathogens in environmental water samples within 30 min. The gLAMP system requires no microfluidic chips and limited personnel training. While the disclosed exemplary embodiments may focus on coliphage (viruses infect bacteria) detection, the gLAMP techniques can also be adapted for the detection and/or monitoring of other microbial pathogens (e.g., *E. coli, Salmonella*) in water or food samples in other settings. The system may also be used for microorganism detection and quantification in other matrixes (e.g., feces, urine, and blood) with simple sample pretreatment (DNA/RNA extraction and purification).

In accordance with exemplary embodiments of the gLAMP techniques, one or more methods and systems are disclosed for detecting target microorganisms (including viral particles, bacterial cells, or target DNA/RNA) in a sample suspected of containing the target microorganisms. The method includes combining loop-mediated isothermal amplification (LAMP) reagents and a hydrogel together with the sample to form a mixture. The hydrogel polymerizes over a short time to immobilize the targets within the mixture. If the targets are present in the sample, amplicons are produced during the heating incubation through LAMP amplification. The targets are detected by visually detecting the presence or absence of the amplicons. The target concentrations may be determined based on the number of fluorescent amplicon dots after the reaction using a smartphone or a fluorescent microscope.

The foregoing summary does not define the limits of the appended claims. Other aspects, embodiments, features, and advantages will be or will become apparent to one with skill in the art upon examination of the following figures and detailed description. It is intended that all such additional features, embodiments, aspects, and advantages be included within this description and be protected by the accompanying claims.

BRIEF DESCRIPTION OF THE FIGURES

It is to be understood that the drawings are solely for purpose of illustration and do not define the limits of the appended claims. Furthermore, the components in the figures are not necessarily to scale. In the figures, like reference numerals designate corresponding parts throughout the different views.

FIG. 3A-F are photographic images showing exemplary amplicon dot profiles resulting from certain experimental in-gel LAMP tests of environmental waters.

FIGS. 4A-B are graphs of example experimental results showing the effects reaction times and template concentrations on results of examples of the in-gel LAMP method.

FIG. 7 is a table showing primer and probe sequences for examples of the in-gel LAMP techniques disclosed herein (SEQ ID NOs:1-11).

DETAILED DESCRIPTION

Figure 1:
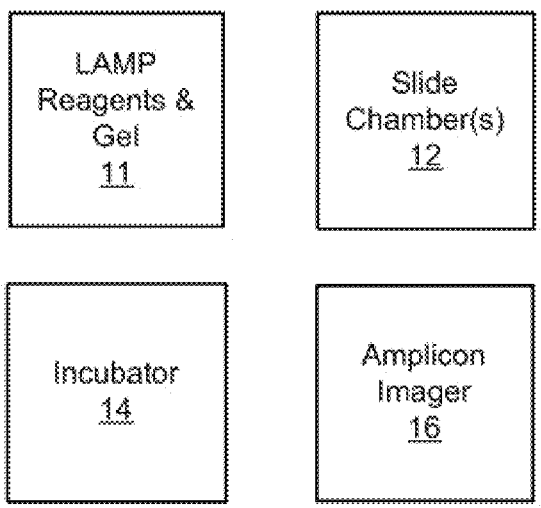
FIG. 1 is a schematic illustration of an exemplary in-gel LAMP assay system.

The following detailed description, which references to and incorporates the drawings, describes and illustrates one or more examples of assay systems, kits and methods based on in-gel loop-mediated isothermal amplification (gLAMP) to test samples. These examples, offered not to limit but only to exemplify and teach embodiments of inventive assays and systems, are shown and described in sufficient detail to enable those skilled in the art to practice what is claimed. Thus, where appropriate to avoid obscuring the invention, the description may omit certain information known to those of skill in the art. The disclosures herein are examples that should not be read to unduly limit the scope of any patent claims that may eventual be granted based on this application.

The word "exemplary" is used throughout this application to mean "serving as an example, instance, or illustration." Any system, method, device, technique, feature or the like described herein as "exemplary" is not necessarily to be construed as preferred or advantageous over other features.

As used in this specification and the appended claims, the singular forms "a," "an," and "the" include plural referents unless the content clearly dictates otherwise.

Although any methods and materials similar or equivalent to those described herein can be used in the practice or testing of the invention(s), specific examples of appropriate materials and methods are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

As discussed above, waterborne diseases are illness caused by pathogenic microorganisms (e.g., viruses, bacteria and protozoa). For example, human pathogenic enteric viruses transmitted through environmental waters are the major cause of many waterborne diseases including hepatitis, gastroenteritis, meningitis, fever, and conjunctivitis. The detection of microbial pathogens in environmental waters is challenging due to their small sizes and large diversities. For instance, direct monitoring of specific viral pathogens is generally impractical for public health protection due to methodological limitations. Similar to bacterial indicators, coliphages (viruses that infect $E.\ coli$) may be used as indicator organisms to predict viral contamination of water. While the disclosed exemplary embodiments may focus on coliphage (viruses infect bacteria) detection, the gLAMP techniques can also be adapted for the detection and/or monitoring of other microbial pathogens (e.g., gram positive and gram negative bacterial species, viruses, and protozoa) in water, clinical or food samples. In addition to environmental waters, the systems and methods disclosed herein may be used for microorganism detection and quantification in other matrixes (e.g., feces, urine, and blood) with sample pretreatment (DNA/RNA extraction and purification).

Loop-mediated isothermal amplification (LAMP or Loopamp) is an isothermal DNA amplification procedure using a set of four to six primers, two to three "forward" and two to three "reverse" that specifically recognize a target DNA sequence (see Nagamine et al., *Nucleic Acids Res.* (2000) 28:e63; Nagamine et al., *Clin. Chem.* (2001) 47:1742-43; U.S. Pat. No. 6,410,278; U.S. Patent Appl. Nos. 2006/0141452; 2004/0038253; 2003/0207292; and 2003/0129632; and EP Patent Appl. No. 1,231,281). Briefly, one set of primers are designed such that approximately of the primer is positive strand the other of the primer sequence is negative strand. After strand displacement amplification by the polymerase, a nucleic acid structure that has hairpin loops on each side is created. From this structure, repeating rounds of amplification occur, generating various sized product. A by-product of this amplification is the formation of magnesium-pyrophosphate, which forms a white precipitate leading to a turbid reaction solution. This presence of turbidity signifies a positive reaction while the absence of turbidity is a negative reaction. Additional additives, such as calcein, allow other visualizations to occur; as for calcein it enables fluorescence detection. The amplification reaction occurs under isothermal conditions (at approximately 65° C.) and continues with an accumulation of 10 copies of target in less than an hour.

Reagents for LAMP are known (e.g., Bst polymerase, dNTPs, buffers etc.). Moreover, primer pairs are easily designed and identified by one of skill in the art using known sequence information. For example, reagent preparations for loop-mediated isothermal amplification of nucleic acids comprises at least one polymerase enzyme, wherein the enzyme is capable of strand displacement, a target-specific primer set, and dinucleotide triphosphates (dNTPs). In some embodiments, the polymerase enzyme capable of strand displacement is Bst enzyme. If the target is RNA, the reagent preparation also includes a reverse transcriptase. In some embodiments, the reverse transcriptase is AMV reverse transcriptase.

The term "microbial" or "microbes" as used herein includes bacteria, fungal, protozoal, and viral organisms. The methods and system of the disclosure can be used to detect and identify the presence of such microbial organisms.

Bacterial microbes that can be detected using the methods and systems of the disclosure include both gram-negative and gram-positive bacteria. For example, bacteria that can be affected include *Staphylococcus aureus, Streptococcus pyogenes* (group A), *Streptococcus* sp. (*viridans* group), *Streptococcus agalactiae* (group B), *S. bovis, Streptococcus* (anaerobic species), *Streptococcus pneumoniae*, and *Enterococcus* sp.; Gram-negative cocci such as, for example, *Neisseria gonorrhoeae, Neisseria meningitidis*, and *Branhamella catarrhalis*; Gram-positive bacilli such as *Bacillus anthracis, Bacillus subtilis, P. acne Corynebacterium diphtheriae* and *Corynebacterium* species which are diptheroids (aerobic and anerobic), *Listeria monocytogenes, Clostridium tetani, Clostridium difficile, Escherichia coli, Enterobacter* species, *Proteus mirabilis* and other sp., *Pseudomonas aeruginosa, Klebsiella pneumoniae, Salmonella, Shigella, Serratia*, and *Campylobacter jejuni*. In particular, the methods and systems of the disclosure are useful for detection of any pathogen. Infection with one or more of these bacteria can result in diseases such as bacteremia, pneumonia, meningitis, osteomyelitis, endocarditis, sinusitis, arthritis, urinary tract infections, tetanus, gangrene, colitis, acute gastroenteritis, impetigo, acne, acne posacue, wound infections, born infections, fascitis, bronchitis, and a variety of abscesses, nosocomial infections, and opportunistic infections.

Fungal organisms may also be detected by the methods and system of the disclosure, e.g., *Microsporum canis* and other *Microsporum* sp.; and *Trichophyton* sp. such as *T. rubrum*, and *T. mentagrophytes*, yeasts (e.g., *Candida albicans, C. Tropicalis*, or other *Candida* species), *Saccharomyces cerevisiae, Torulopsis glabrata, Epidermophyton floccosum, Malassezia furfur* (*Pityropsporon orbiculare*, or *P. ovale*), *Cryptococcus neoformans, Aspergillus fumigatus, Aspergillus nidulans*, and other *Aspergillus* sp., Zygomycetes (e.g., *Rhizopus, Mucor*), *Paracoccidioides brasiliensis, Blastomyces dermatitides, Histoplasma capsulatum, Coccidioides immitis*, and *Sporothrix schenckii*.

Viral organisms that can be detected by the method and systems of the disclosure include, but is not limited to, human immunodeficiency virus (HIV), Junin Virus, BK virus, Machupo virus, Varicella zoster virus, alphavirus, Colorado tick fever virus, rhinoviruses and coronaviruses, cytomegalovirus, Dengue viruses, Ebolavirus, Enterovirus sp., Herpes simplex-1, -2, Hepatitis-A, -B, -C, -D, -E viruses, Measles virus, Mumps virus, Norovirus, respiratory syncytial virus, Rotavirus, Rubella virus, SARS coronavirus, West Nile Virus and Zika Virus.

FIG. 1 is a schematic illustration of an exemplary in-gel LAMP (gLAMP) assay system 10, which enables microbial pathogen quantification, e.g., coliphage quantification, within about 30 minutes using standard laboratory devices. The system 10 may be a kit that includes LAMP reagents and a polymer gel 11; one or more chambers 12 that include at least one slide for viewing a mixture of the LAMP reagents, gel and sample; an incubator 14 for heating the mixture placed on the slides; and an imager 16 for viewing the amplification products, e.g., amplicon dots, resulting from the LAMP reaction in the chamber 12.

The hardware included in the system 10 may include standard laboratory devices, in some embodiments. The LAMP reagents may include, consist of, or consist essentially of any suitable LAMP reagents for initiating and completing a LAMP reaction, for example, those described herein below. The slide chamber 12 may include any suitable chamber for holding and viewing the mixture, for example, a PCR frame seal chamber. The incubator 14 may be any suitable means for heating the mixture for the desired period of time at the desired temperature(s). For example, the incubator may include a PCR machine (MJ Research PTC-100) or a mini dry bath (Benchmark, Edison, N.J.). Alternatively, simple water bath can be used as a heat source for the incubator 14. The amplicon imager 16 may include any suitable means for visually inspecting the processed mixture; for example, the imager 16 may include an illumination source, means for dying or marking amplification products in the mixture, and a camera or microscope for capturing images of the illuminated slide presenting the processed mixture. For example, the illumination source may be an inexpensive blue (460-470 nm) LED pen used to illuminate the slides or a gel imager.

Generally, during operation of the assay system 10 target microorganisms (e.g., MS2, *E. coli, Salmonella* and *Enterococcus*) are immobilized with LAMP reagents within a polymer gel, for example, a hydrogel such as one or more polyethylene glycol (PEG) hydrogels, and then the viral RNAs are amplified through an in situ LAMP reaction. Due to the restriction effect of the polymer gels, one target microorganism may only produce one amplicon dot. Therefore, the sample microorganism concentrations can be determined based on the number of fluorescent amplicon dots after the reaction using the amplicon imager 16, e.g., smartphone or a fluorescent microscope.

The gLAMP assay is significantly faster than other available methods taking less than 30 minutes, compared to 2-4 hours for qPCR and more than 24 hours for traditional culture-based methods. The amplified gel slides can be stored at room temperature for more than one month without affecting the florescent dots visualization. This indicates that the gel matrix provides a good protection for the amplicons, which would allow for sample shipment in case further analysis is required. Considering its outstanding simplicity, sensitivity, and rapidity, the gLAMP techniques disclosed herein hold great potential for microbial water quality analysis, especially in resource-limited settings.

Furthermore, example experimental results demonstrated that the gLAMP assay results were shown to correlate well with traditional plaque assay counts ($R^2=0.984$, $p<0.05$) and achieved similar sensitivity to real time quantitative polymerase chain reaction (RT-qPCR) (1 PFU/reaction). Moreover, experimental results showed that the gLAMP technique demonstrated a high tolerance against inhibitors present in toilet wastewater, in which RT-qPCR was completely inhibited. Considering its simplicity, sensitivity, and rapidity, gLAMP present a vastly improved technique for microbial water quality analysis, especially in resource-limited settings.

The gLAMP assay system 10 may also be useful for other water testing/monitoring applications or food sample applications.

Figure 2:
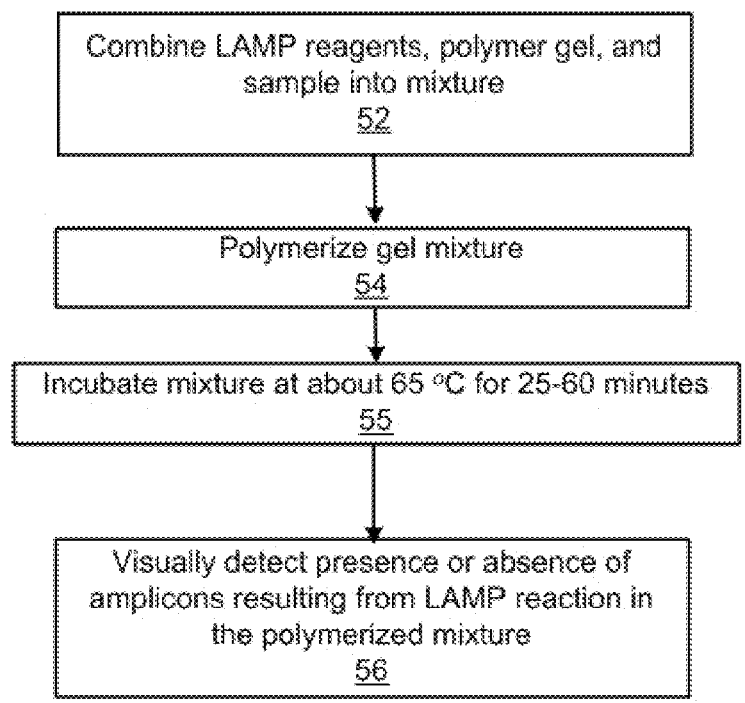
FIG. 2 is a flowchart diagram illustrating an exemplary in-gel LAMP method of detecting viral particles and/or microbial pathogens in a sample.

FIG. 2 is a flowchart diagram illustrating an exemplary in-gel LAMP (gLAMP) method 50 of detecting/monitoring viral particles and/or microbial pathogens in a sample. In step 52, LAMP reagents, the gel and a sample are combined in a mixture. The sample may be an environmental sample or clinical sample. For example, the sample include environmental water, soil, feces, urine, blood, or any combination of the foregoing.

The gel may include, consist of, or consist essentially of any suitable polymer gel or combinations of different gels. For example, in some exemplary embodiments, the polymer gel acting as the matrix for gLAMP may be a polyacrylamide gel. For example, the polyacrylamide gel may be formed through the crosslinking between acrylamide and bis-acrylamide (40% (w/v) solution Acrylamide/Bis 19:1) (Bio-Rad, Hercules, Calif.) using ammonium persulfate (Bio-Rad, Hercules, Calif.) as initiator catalyzed by tetramethylethylenediamine (TEMED) (Bio-Rad, Hercules, Calif.). In other exemplary embodiments, the polymer gel acting as the matrix for gLAMP may be a polyethylene glycol (PEG) hydrogel. For example, a PEG gel may be formed through Michael addition between the four-arm PEG acrylate (molecular weight (MW) 10K) and thiol-PEG-thiol (MW 3.4K) (Laysan Bio, Arab, Ala.) at mole ratio of 1:2.

In an exemplary embodiment of the gLAMP assay, 25 µL of a hydrogel reaction mix may include, consist of, or consist essentially of: 12.5 µL 2× WarmStart® LAMP mastermix (New England Biolabs, Ipswich, Mass.), 1.25 µL 20× virus primer mix (Table shown in FIG. 7), 0.8 µL quencher primer (qFIP-3'IBFQ) when fluorophore labeled primer (5'FAM-FIP). For experimental samples, 2 µL MS2 RNA templates or 2 µL of a raw water sample may be used. The hydrogel may be added to reaction mix at the final concentration of 10% (w/v). The above 25 µL hydrogel reaction mix may be loaded into an in situ PCR frame seal chamber (9×9 mm) (Bio-Rad, Hercules, Calif.) on a glass slide and then covered with a transparent qPCR film (Sorenson, Salt Lake City, Utah). The hydrogel may then be polymerized at room temperature (21° C.) for 5-15 minutes (step 54) and then incubated on a PCR machine (MJ Research PTC-100) or a mini dry bath (Benchmark, Edison, N.J.) at about 65° C. for between 25-60 minutes, for example, 25 minutes (step 55).

After amplification, the gel mixture may then be optionally stained with 0.5× LAMP dye (included in the WarmStart® LAMP kit) in the dark for 15 minutes, and then washed twice with 2×TE buffer (pH=7.8). For reactions using the complementary fluorescent probe and quencher primers (as described below), post-reaction staining is not necessary.

In step 56, the presence or absence of amplification products, e.g., amplicons, in the polymerized mixture is visually determined. To do this, the slides may be illuminated with a E-Gel™ Safe Imager (Invitrogen, Carlsbad, Calif.) and the amplicon dots are documented with a smart phone (e.g., an iPhone 6s plus or similar smart phone). Alternatively, the slides may be visualized using a fluorescence microscope (e.g., a Leica DMi8, Leica Co., Germany).

For demonstrating the efficacy of the assay system 10 and method 50, a model coliphage was prepared. The coliphage MS2 (ATCC 15597-B1) was chosen as model virus for the method development. For phage propagation, 0.1 mL ($10^7$ PFU/mL) of MS2 was inoculated into 20 mL of actively growing E. coli-3000 (ATCC 15597) host suspension in Luria-Bertani medium. The infected bacteria were continuously aerated at 37° C. for 36 hours. The host-associated MS2 suspension was then centrifuged at 3,000×g for 10 minutes to pellet the bacterial cells and debris. The supernatant, containing the MS2 virions, was further purified by 0.2 µm syringe filter (GE Whatman, Pittsburgh, Pa.). The filtrate was diluted 1,000× in 1×PBS (pH=7.5) and used as MS2 stock for seeding studies. The concentration of MS2 stock was titrated by the double agar layer method. AllPrep PowerViral DNA/RNA Kit (Qiagen, Germantown, Md.) was used for MS2 RNA extraction as per manufacturer's protocol.

In embodiments of the gLAMP assay using polyacrylamide gels, clear polyacrylamide gels may be formed relatively quickly, within 10-15 minutes. In embodiments of the gLAMP assay using PEG gels, the formation of PEG gel may be generally faster, taking only 3-5 minutes at alkaline pH (the pH of the LAMP reaction mix may be about 8.8). Both types of gel typically show no fluorescent background and the gLAMP assay may be successfully carried out in either case (see FIG. 3).

FIG. 3 are photographic images showing exemplary amplicon dot profiles resulting from certain experimental gLAMP tests of environmental waters. Photos A and B of FIG. 3 show amplicon dots for during an assay experiment using polyacrylamide hydrogel. Photos C-F of FIG. 3 show amplicon dots for during an assay experiment using a PEG hydrogel. In photos A-D, the amplicons were stained with 0.5× LAMP dye after incubation, and in photos E-F QUASR primers were used without post-reaction staining. Photos A, C, E were taken by a fluorescence microscope, and photos B, D, F were taken by an iPhone 6S Plus. The assay reaction time for the images was 25 minutes.

When the amplicon dot size is smaller than 20 µm (diameter), their detection may require a fluorescence microscope. To facilitate the results reading with a smartphone camera while still maintain a practical assay dynamic range, dot size of 50-200 µm may be used. The size of amplicon dots may be mainly determined by the restriction effect of the gel matrix.

In some embodiments of the assay, the gel matrix may be formed to allow the free diffusion of small molecules (MW<100 kDa) such as water, ions, primers (<50 bp, MW<15 kDa), and enzymes (Bst=67 kDa), but restrict the spread of DNA/RNA templates/amplicons (>150 bp, MW>100 kDa). This may be achieved by manipulating the gel crosslinking degree to tune key parameters such as mesh size and molecular weight between crosslinkers in order to change macroscopic properties (i.e., diffusion). Prior studies have found that 514 bp, 234 bp and 120 bp templates produced uniform PCR amplicon dots of 100 µm, 400 µm and 800 µm in polyacrylamide hydrogel, respectively. It should be noted that, unlike the single length PCR amplicons, products of LAMP are a mixture of concatemers of the target region with various sizes. Based on the agarose gel electrophoresis profile, the shortest MS2 LAMP amplicons may be about 90 bp, while the longest amplicons may be up to several thousand bp. During a gLAMP assay, longer amplicons may be retarded by the hydrogel, but shorter may amplicons diffused away from the initial templates (the center of the dot), and serve as templates for further amplification until they reach the diffusion limit or the LAMP reagents (e.g., enzyme, primer, dNTP) in their vicinity are depleted. Due to the stochastic nature of LAMP, dots of different size may be produced in the hydrogels.

The mesh size of polyacrylamide and PEG hydrogels may be similar and in the range of 20-25 nm. However, the amplicon dots in the PEG gel (e.g., see FIG. 3, photo C) may be smaller and more uniform than those formed in polyacrylamide gel (FIG. 3, photo A). Thus, the PEG gel may have a better restriction on the smaller amplicons. Therefore, besides size exclusion, other interactions (i.e., charge interaction) between the polymers and the DNA templates may also affect the diffusion coefficient.

Clear amplicon dot profiles may be obtained through post-reaction gel staining with, for example, an intercalating LAMP dye (FIG. 3 photos A, B). This highlights the feasibility of adapting traditional qualitative LAMP assays targeting other microorganisms (e.g., *E. coli, Enterococcus*, and *Salmonella*) into quantitative assays via the gLAMP technique.

In some embodiments, normal LAMP primers may be used in post-staining the gLAMP mixture. Referring to FIG. 7, the final concentration of F3/B3, FIP/BIP and LF/LB may 0.2 µM, 1.6 µM, and 0.4 µM, respectively.

In another embodiment of the gLAMP assay, a primer-dye/primer-quencher duplex, also known as QUASR (quenching of unincorporated amplification signal reporters), may be used to mark amplification products, without the need for post-reaction staining. In QUASR, the forward internal primer (FIP) is labeled with a fluorophore at the 5' prime end (5'FAM-FIP). The probe is quenched by a complementary primer with a quencher (Iowa Black® FQ) at the 3' prime end (qFIP-3'IBFQ). As the melting temperature ($T_m$) of the complex is 5-10° C. lower than the reaction temperature (65° C.), the 5'FAM-FIPs are released and behave like regular FIPs during the LAMP reaction. 5'FAM-FIPs are incorporated into the LAMP amplicons when there are target templates present in the sample. After the reaction, free flow 5'FAM-FIPs are quenched again by the complementary quencher primer qFIP-3'IBFQs. In contrast, 5'FAM-FIPs incorporated into LAMP amplicons would not be quenched, as they already form a stable double strand DNA structure during LAMP reaction.

For QUASR probe, fluorophore (FAM) may be attached to the FIP at 5' end; quencher IBFQ may be attached to the quench probe qFIP at the 3' end. IBFQ may be Iowa Black® FQ (Integrated DNA Technologies, Coralville, Iowa), which has a broad absorbance spectrum ranging [from 420 to 620 nm with peak absorbance at 531 nm. This quencher may be used with fluorescein and other fluorescent dyes that emit in the green to pink spectral range. In QUASR gLAMP, FIP (FIG. 7) may be substituted by 5'FAM-FIP and 2× qFIP-3'IBFQ (3.2 µM) may be added to the reaction mix.

Compared to unspecific DNA intercalating dyes (i.e., the LAMP dye), QUASR significantly reduces the issue of false positive associated with LAMP assays. However, QUASR cannot turn into a quantitative assay in a real-time LAMP scheme, because the fluorescent intensity of the reaction mix is constantly at the highest level (all 5'FAM-FIP released) instead of progressively increasing during heat incubation. Therefore, it can only be used as a qualitative assay for endpoint determination.

A higher concentration of quencher primer (2× of the complementary probe primer) may be used to maintain a clean gel background at the end of the gLAMP reaction in some embodiment of the gLAMP assay. The PEG gel may allow the free movement of the dye-labeled short oligonucleotides, even though the diffusion coefficient may be smaller in the gel than that in a solution. As 5'FAM-FIPs are incorporated into the amplicons and accumulated around the initial templates, bright and defined amplicon dots may be directly visualized with a smartphone camera upon blue light exposure.

FIGS. 4A-B are graphs of example experimental results showing the effects reaction times and template concentrations on QUASR amplicon dot results of exemplary gLAMP methods. gLAMP assay experiments were carried out using extracted MS2 viral RNA. The graphs show box plots of amplicon dot diameters on the left sides. Different letters (a, b, c) indicate significant differences at the p, 0.05 level according to one way ANOVA followed by Tukey's post hoc test. For the graph of FIG. 4A, the template concentrations are defined as follows: low=1-20 copies/gel, medium=20-200 copies/gel, and high=200-2000 copies/gel. Medium template concentration was used for the graph of FIG. 4A, and the reaction time for graph of FIG. 4B was 25 minutes. Extracted MS2 RNA were used as templates in the sample.

The experimental results show that amplicon dots were visible as early as 20 minutes under a fluorescent microscope (FIG. 4A). The dots developed to about 156±33 µm (diameter) after 25 min and the fluorescent intensity was strong enough to be detected with a smartphone camera (FIG. 3). Although the amplicon dots kept increasing in size and reached 212±50 µm after 30 minutes, the dot counts stayed similar to those at 25 minutes. Hence, 25 minutes may be a desirable reaction time for an exemplary MS2 gLAMP assay. The amplicon dot size showed no significant difference at low (1-20 copies/gel) and medium template (20-200 copies/gel) concentrations (FIG. 4B). Under these conditions, amplicon dots were relatively far from each other and had limited interactions. The dot size represented the largest size the amplicons could develop within the given reaction time, while the size variability in a single gel may result from variable initial template conformation, the degree of template denaturation, or from local inhomogeneities in the hydrogel structure (due to free dangling ends, self-looping or entanglements of macromers). In contrast, the size of amplicon dots at high concentration (200-2000 copies/gel) were significant smaller than those formed at the low and medium concentration (FIG. 4B). The smaller amplicon size at higher template concentration may be due to a global auto-inhibition, especially due to a drop in pH. Local competition for enzymes, primers, and dNTP may also contribute, as clear separations were developed among the amplicons close to each other. The smaller amplicon sizes plus the watershed developed at higher template concentration may benefit the assay's dynamic range by improving fluorescent dot identifiability. For smartphone camera reading, the assay dynamic range may be 1-1000 dots/gel. When using a fluorescence microscope for results reading, each gel may accommodate as many as 5000 dots without compromising the precision.

In some embodiments of the gLAMP assay, manual amplicon counting may be used. In other embodiments of the gLAMP assay, automatic amplicon analysis for microscope and smartphone images may be performed by an automatic amplicon counter, such as CellProfiler 2.2.0. With appropriate threshold setting, the difference between automatic and manual counting may be less than 5%.

In some embodiments of the gLAMP assay, nucleic acid extraction and purification may be performed on the sample prior to the LAMP reaction. Nucleic acid extraction and purification are usually required in qPCR assays to improve the detection. Many commercial extraction kits have optimized the procedure providing high-quality DNA/RNA for downstream qPCR analysis, and these kits may be used with gLAMP techniques. However, the process takes 30-90 minutes and these kits are relatively expensive.

In other embodiments of the gLAMP assay, heating pretreatment may be applied to the sample prior to the LAMP reaction. In some embodiments of the gLAMP assay, direct detection of viral particles is achieved in unprocessed samples, without prior nucleic acid extraction or preheating treatment.

Figure 5A:
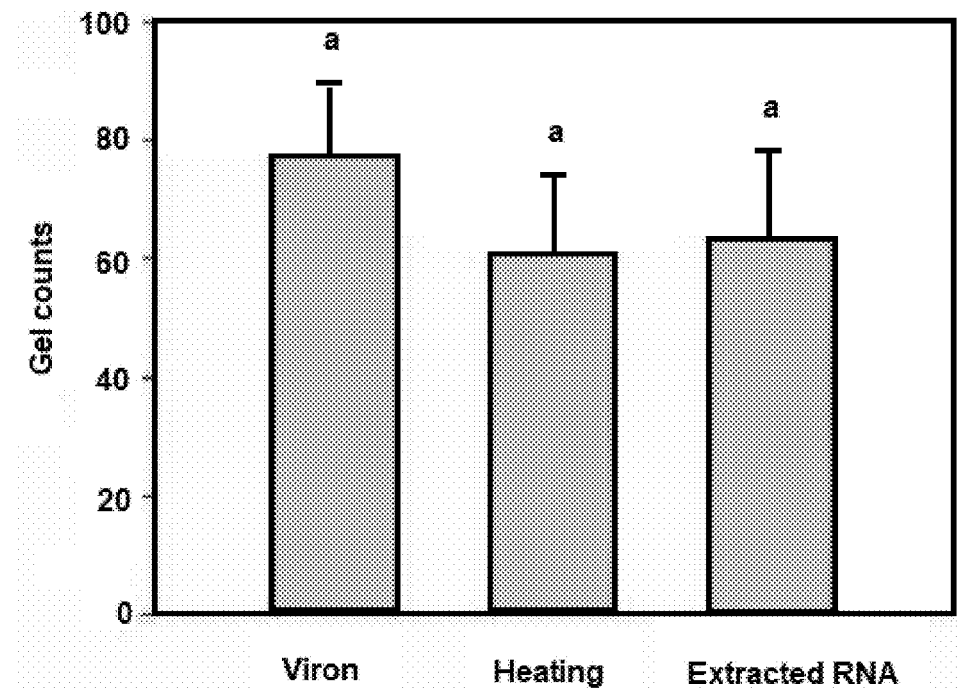
FIGS. 5A-B are graphs of example experimental results showing (FIG. 5A) the effects of certain sample pretreatments on examples of the in-gel LAMP method and (FIG. 5B) count comparisons between an example of the in-gel LAMP method and a conventional plaque assay.
Figure 5B:
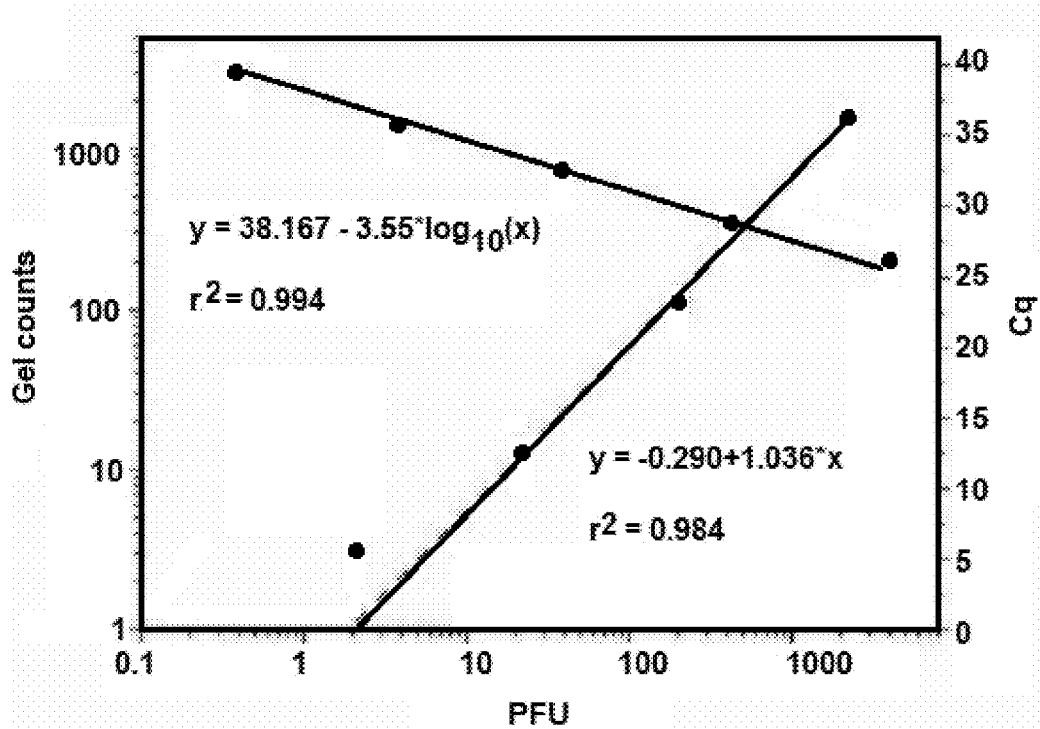

FIGS. 5A-B are graphs of example experimental results showing the effects of certain sample pretreatments on examples of the gLAMP methods (FIG. 5A) and count comparisons between an example of the gLAMP method and a conventional plaque assay (FIG. 5B).

Referring to FIG. 5A, this graph shows experimental results of gLAMP methods employing various sample pretreatments. In the graph of FIG. 5A, Virion refers to direct detecting of viral particles without sample pretreatment; Heating indicates that the sample was preheated to 95° C. for 5 minutes of denaturation; and Extracted RNA indicates extracted RNA pretreatment using a commercially-available AllPrep Power Viral DNA/RNA kit. These experiments were carried out in phosphate-buffered saline (PBS); therefore, the role of the extraction kit was solely to release the viral RNA. The purification effect was limited, as very low concentrations of inhibitors were expected in the buffered system. FIG. 5A demonstrates that direct gLAMP assay (with no sample pretreatment) obtained similar amplicon counts in comparison to heating pretreatment gLAMP assay and the gLAMP assay using samples pretreated with a commercial viral RNA extraction kit. No significant difference was found in terms of amplicon dot size and fluorescent intensity between these treatments. Simple heating pretreatment was previously reported to improve the detection of bacteria in LAMP assays, as the compromised cell membranes were more permeable to LAMP reagents and the denatured DNA can facilitate the strand displacement activity of the Bst enzyme. However, the presented results indicate that the LAMP primers and enzymes (RTx reverse transcriptase and Bst 2.0 DNA polymerase) were able to penetrate the viral capsid at the reaction temperature (65° C.), and the denaturing heating step may not be necessary as the viral genome is much smaller compared to that of bacteria.

To evaluate the sensitivity of direct gLAMP, it may be compared with traditional plaque assay and RT-qPCR (as shown by the graph of FIG. 5B). The direct gLAMP assay amplicon counts showed a good correlation to plaque assay counts ($R^2=0.984$, $p<0.05$). The regression line (slope=1.036, intercept=−0.290) indicates that 1 gel amplicon dot was closely equal to 1 plaque forming unit (PFU). The direct gLAMP Assay achieved a similar lower detection limit (0.7 PFU/reaction) compared to that of RT-qPCR (0.4 PFU/reaction), while RT-qPCR still showed the advantage of a larger upper detection limit. The assay sensitivity and dynamic range were compared with RT-qPCR using Eppendorf RealPlex2 (Hamburg, Germany).

The dynamic range of the gLAMP assay may be increased by reducing the amplicon dot size. Accommodating more amplicon dots in a single gel may be desirable for applications such as mutation detection and in-gel sequencing. However, the ability to distinguish amplicon dots from other contaminating fluorescent signals (contaminating DNA/RNA fragments or particles) may suffer at small dot sizes. Consequently, the precision at low concentration (<20 copies/reaction) would be compromised. For environmental monitoring purpose, the concentrations of MS2 in water samples are rarely above the upper detection limit of the disclosed gLAMP ($10^6$ PFU/mL) assay. Moreover, high concentration samples can be easily diluted. In fact, concentrating small amount of MS2 from large volumes of water samples (e.g., groundwater) is much more challenging. Therefore, maintaining the precision at low concentration may be valuable to the disclosed gLAMP assays.

Figure 6A:
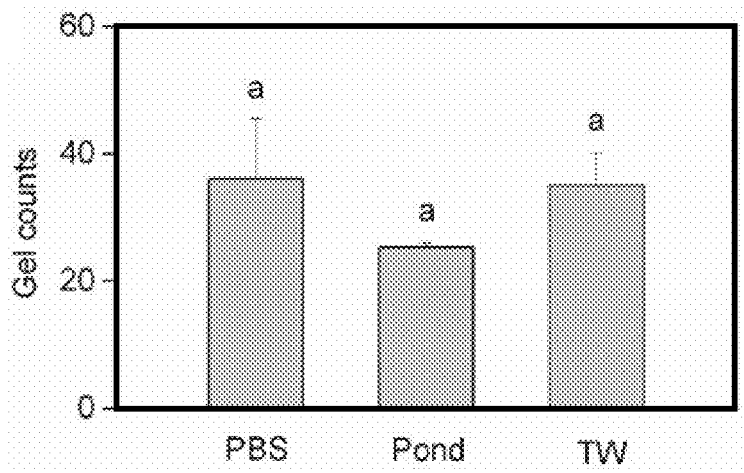
FIGS. 6A-C are graphs of example experimental results of exemplary direct gLAMP assays in processing certain environmental water samples.
Figure 6B:
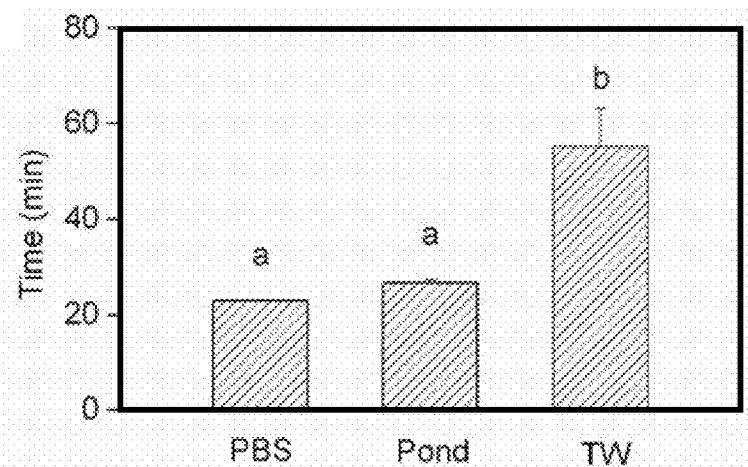
Figure 6C:
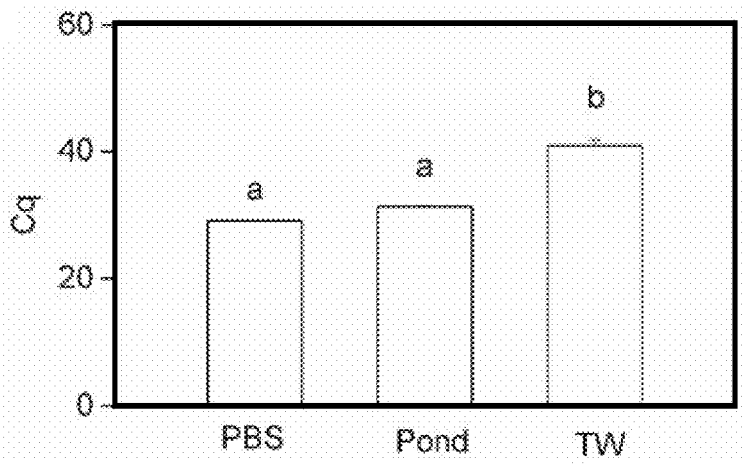

FIGS. 6A-C are graphs of example experimental results of exemplary direct gLAMP assays used to process certain environmental water samples. Enzyme driven nucleic acid amplification processes are susceptible to various inhibitory substances (e.g., organic matter and heavy metals) commonly found in environment samples. An example of the direct gLAMP assay was tested using: toilet wastewater that was yellow-brownish and had a chemical oxygen demand (COD) level of 821 mg/L representing highly contaminated water; pond water that was clear and less contaminated (COD=75 mg/L); and a PBS control. Direct gLAMP assays were successfully carried out in both MS2-spiked environmental water samples (toilet water and pond). No significant differences were observed compared to control experiments in PBS buffer, in terms of amplicon dot counts ($p>0.05$) (FIG. 6A) as well as dot morphologies. In contrast, minor inhibition was observed in the gLAMP assay for pond water as the time-to-detection was delayed from 23 min in PBS to 27 min in pond water. In general, LAMP assays have a more robust chemistry than PCR for handling complex samples because: (1) they employ six primers to initiate the amplification compared to two primers in PCR; (2) the smaller 67 kDa Bst polymerase used in LAMP may enter target cells/viral particles more easily than the 94 kDa Taq DNA polymerase used in PCR; and (3) the yields of LAMP (10-20 μg/reaction) are about 50-100 times higher than those of PCR (0.2 μg/reaction). However, some known LAMP assays are qualitative or semi-quantitative. The use of crude samples may not compromise the lower detection limit (still detectable), but it usually resulted in an increase in the time-to-detection or a decrease in the signal-to-noise ratio at the end of the reaction.

The concentration of humic-like dissolved organic matter (DOM) in toilet wastewater may be 10-15 times higher than that in pond water. The toilet wastewater also may also contain low levels of proteinaceous material, and the inhibitors in toilet wastewater are likely to be organic origin, similar to those found in urine and feces samples. Urea present in urine samples is known to prevent the noncovalent binding of polymerase enzymes and interferes with primer annealing. The tolerance of LAMP to urea was reported to be up to 1.8 M. Inhibitors derived from feces are highly variable, depending on nutrition, gut flora and lifestyle. Complex polysaccharides, bile salts, lipids, and urate found in stool samples are particularly responsible for PCR inhibition. The inhibition mechanisms are complicated including binding to polymerase (complex polysaccharides, bile salts), competition with templates (bilirubin) and chelation of the amplification cofactor $Mg^{2+}$ (phytic acid).

The better performance of gLAMP assays in toilet wastewater when compared to PCR methods may be attributed to the gel matrix may have a more significant role in the enhanced tolerance against inhibitors in toilet wastewater. First, similar to digital PCR, a gLAMP assay is an endpoint amplification detection assay by counting the final amplification products, therefore, its quantification is less affected by amplification efficiency. Second, since the DNA/RNA templates are spatially isolated in the gLAMP assays, interference between DNA/RNA molecules and substrate competition during amplification may be minimized. Moreover, depending on their molecular weight, the movements of large molecular weight organic inhibitors may be restricted by the gel matrix, and thus, the local inhibitor concentrations close to the templates may be reduced.

Any of the assay systems, e.g., system 10, or methods, e.g., method 50, disclosed herein may be employed for efficient detection and/or monitoring of microorganisms such as viral particles, viruses, bacteriophages, protozoa, bacteria, or any combination of the foregoing, and the like in any suitable sample, for example, a water or food sample, or biological sample.

EXAMPLES

Model Coliphage MS2 Preparation.

Coliphage MS2 (ATCC 15597-B1) was chosen as the model virus for the method development. For phage propagation, 0.1 mL [$10^7$ plaque-forming units (PFU)/mL] of MS2 was inoculated into 20 mL of actively growing $E.$ $coli$-3000 (ATCC 15597) host suspension in Luria-Bertani medium. The infected bacteria were continuously aerated at 37° C. for 36 h. The host associated MS2 suspension was then centrifuged at 3000 g for 10 min to pellet the bacterial cells and debris. The supernatant, containing the MS2 virions, was further purified by 0.2 μm syringe filter (GE Whatman, Pittsburgh, Pa.). The filtrate was diluted 1000× in 1× PBS (pH of 7.5) (Corning, N.Y., N.Y.) and used as MS2 stock for seeding studies. The concentration of MS2 stock was titrated by the double-agar layer method. An AllPrep PowerViral DNA/RNA Kit (Qiagen, Germantown, Md.) was used for MS2 RNA extraction per the manufacturer's protocol.

gLAMP Assay Design.

Two types of hydrogels were initially tested as the matrix for gLAMP. The polyacrylamide (PA) gel was formed through the cross-linking between acrylamide and bis-acrylamide (acrylamide/Bis 19:1) (BioRad, Hercules, Calif.) using 0.05% (w/v) ammonium persulfate (Bio-Rad, Hercules, Calif.) as initiator and catalyzed by 0.05% (w/v) tetramethylethylenediamine (TEMED) (Bio-Rad). The PEG gel was formed through Michael addition between the four-arm PEG acrylate [molecular weight (MW) of 10000] and thiol-PEG-thiol (MW of 3400; Laysan Bio, Arab, Ala.) at a mole ratio of 1:2. The MS2 LAMP primers and probes originally developed by Ball et al. were used and optimized in the current study. For each gLAMP assay (25 μL), the optimized hydrogel reaction mix had the following composition: 10% (w/v) hydrogel, 12.5 μL of 2× WarmStart LAMP Mastermix (a blend of Bst 2.0 WarmStart DNA polymerase and WarmStart RTx reverse transcriptase; New England Biolabs, Ipswich, Mass.), 1.25 μL of 20× virus primer mix (the final concentrations of F3/B3, FIP/BIP and LF/LB were 0.2, 1.6, and 0.4 μM, respectively), and 2 μL of MS2 RNA templates or 2 μL of water sample. For reactions using the complementary fluorescent probe and quencher primers, quencher primer (qFIP-3'IBFQ) was added (final concentration 3.2 μM) when fluorophore-labeled primer (5' FAM-FIP) was used to substitute the regular FIP primer. The above-described 25 μL of hydrogel reaction mix was loaded into an in situ PCR frame seal chamber (9×9 mm; Bio-Rad) on a glass slide and then covered with a transparent qPCR film (Sorenson, Salt Lake City, Utah). The hydrogel was polymerized at room temperature (21° C.) for 5-15 min and then incubated on a PCR machine (MJ Research PTC-100, Watertown, Mass.) or a mini dry bath (Benchmark, Edison, N.J.) at 65° C. for 25 min. After amplification, the gel was stained with 0.5× LAMP dye (included in the WarmStart LAMP kit) in the dark for 15 min and then washed twice with 2×TE buffer (pH of 7.8; Corning, N.Y., N.Y.). For reactions using the complementary fluorescent probe and quencher primers, no post-reaction staining was needed. The slides were illuminated with an E-Gel Safe Imager (Invitrogen, Carlsbad, Calif.), and the amplicon dots were documented with an iPhone 6s Plus. To verify the sensitivity of the smartphone detection system, the slides were also imaged using a fluorescence microscope (Leica DMi8; Leica Co., Germany).

gLAMP Assay Optimization.

Initial gLAMP development was carried out using extracted MS2 viral RNA. Assays were conducted to find the optimal staining strategy (post-reaction staining with LAMP dye or using fluorescent probe), incubation time (20, 25, and 30 min), and assay dynamic range (low, 1-20 copies per reaction; medium, 20-200 copies per reaction; and high, 200-2000 copies per reaction). Subsequently, with the intention of simplifying the RNA extraction step, we also explored simple heating (95° C., 5 min) as a pretreatment procedure or direct detection of MS2 viral particles without RNA extraction. The assay sensitivity and dynamic range were compared to RT-qPCR using Eppendorf RealPlex2 (Hamburg, Germany).

Tolerance of gLAMP to Inhibitors Present in Environmental Water Samples.

A total of three environmental water samples were tested to evaluate the tolerance of gLAMP to inhibitors naturally present in environmental waters. Lake water (LW) was collected from Echo Park Lake (Los Angeles, Calif.), which functions primarily as a detention basin in the city's storm-drain system while providing recreational benefits and wildlife habitat. Pond water (PW) was collected from the Turtle Pond at the California Institute of Technology (Caltech). Wastewater (WW) was collected from the sedimentation and storage tank of a pilot scale solar-powered mobile toilet system also located on the Caltech campus. WW is composed of urine, feces, and handwashing and toilet-flushing water. More details about the design and operational conditions of the toilet system were reported in previous studies (Huang et al., Water Res., 92:164-172, 2016; Cho et al. Environ. Sci. Technol., 48(4):2377-2384, 2014). Basic water-quality parameters of these samples are summarized in Table 1.

TABLE 1

Water quality parameters of environmental samples:

| | Lake Water | Pond Water | Toilet Wastewater | Primary Effluent |
|---|---|---|---|---|
| pH | 8.45 | 7.75 | 9.16 | 8.02 |
| EC (mS/cm) | 0.794 | 0.926 | 14.59 | 1.377 |
| COD (mg/L) | 60 | 74.7 | 821.3 | 1110 |
| DOC (mg/L) | 30 | 101 | 430 | 352 |

The dissolved organic matter (DOM) in the environmental samples were characterized by excitation-emission matrix (EEM) using a fluorescence spectroscopy (Shimadzu RF-6000, Kyoto, Japan). Corrected EEMs were generated from raw scans (excitation wavelengths: 250-550 nm, 5 nm interval; emission wavelengths: 300-600 nm, 2 nm interval) and used to estimate the various DOM components. The concentrations of indigenous MS2 (without preconcentration) in all these samples were below the detection limit of plaque assays (1 PFU/mL) and RT-qPCR (1 plaque-forming unit per reaction). Therefore, pure cultured MS2 was spiked to these samples and a PBS buffer solution at the final concentration of $2\times10^3$ to $2\times10^4$ PFU/mL (equaling 10-100 plaque-forming unit per reaction). Spiked water samples were allowed to equilibrate for 1 h before being directly analyzed with gLAMP, in-tube realtime LAMP, and RT-qPCR without RNA extraction. The MS2-spiked PBS served as a control because no inhibition was expected in this buffer solution. Inhibition effect was evaluated by comparing results from environmental samples with those obtained from PBS: in gLAMP, inhibition was reflected as fewer fluorescent dot counts in environmental samples than those in PBS, while for in-tube LAMP and qPCR, it was shown as increased time-to detection and larger quantitation cycle (Cq) values, respectively.

Detection of MS2 in Primary Effluent Samples.

To demonstrate the detection of MS2 in non-spiked natural water, primary effluent wastewater sample was collected from a local wastewater treatment plant serving 150000 people. A 20 mL water sample was filtered with 0.22 μm syringe filters (GE Whatman, Pittsburgh, Pa.) to remove bacteria and debris before further analysis. For double-layer plaque assays, F-specific coliphages were enumerated using *E. coli* Famp (ATCC 700891) as the bacterial host, while *E. coli* C3000 (ATCC 15597) was used for total (somatic and F-specific) coliphage enumeration. A total of 15 mL of the filtrate was further concentrated to 150 μL using an Amicon Ultra-15 Centrifugal Filter (30 KDa nominal molecular weight limit) (Millipore, Burlington, Mass.). Virus RNA was extracted from 100 μL of concentrate using the AllPrep PowerViral DNA/RNA Kit (Qiagen, Germantown, Md.) and then analyzed by gLAMP and RT-qPCR.

Gel Selection.

Clear polyacrylamide gels were formed within 10-15 min, while the formation of PEG gel was faster, taking 3-5 min at alkaline pH (the pH of the LAMP reaction mix is 8.8). Both gels showed no fluorescent background, and gLAMP was successfully carried out in either case. Experiments showed that when the amplicon dot sizes were smaller than 20 μm (diameter), the detection would require a fluorescence microscope. To facilitate the results reading with a smartphone camera while still maintaining a practical assay dynamic range, dot sizes between 50 to 200 μm were used in the current study. The size of amplicon dots was mainly decided by the restriction effect of the gel matrix. Ideally, the gel matrix should allow the free diffusion of small molecules (molecular weight (MW) of <100 kDa) such as water, ions, primers (<50 bp, MW<15 kDa), and enzymes (Bst: 67 kDa) but restrict the movement of DNA and RNA templates and the amplicons (>150 bp, MW>100 kDa). This can be achieved by tuning the gel cross-linking degree and the length of cross-linkers to control the gel mesh size and, thus, the macroscopic gel properties (i.e., diffusion). It should be noted that, unlike single length PCR amplicons, products of LAMP are a mixture of concatemers of the target region with various sizes. Based on the agarose gel electrophoresis profile, the shortest MS2 LAMP amplicons were about 90 bp, while the longest amplicons were up to several thousand base pairs. During gLAMP, longer amplicons were retarded by the hydrogel matrix, but shorter amplicons diffused away from the initial templates (the center of the dot) and served as templates for further amplification until they reached the diffusion limit or the LAMP reagents (e.g., enzyme, primer, and dNTP) in the vicinity were depleted. Due to the stochastic nature of LAMP, dots of different sizes were produced in the hydrogels. According to previous studies, the mesh size of the 2 hydrogels were similar and in the range of 20-25 nm. However, the amplicon dots in the PEG gel were significantly smaller and more-uniform than those formed in polyacrylamide gel. The results showed that the PEG gel had a better restriction effect on the smaller amplicons. Therefore, besides size exclusion, other interactions (i.e., charge interaction) between the polymers and the DNA templates may also affect the diffusion coefficient. Given the better template-restriction effect, PEG hydrogel was chosen for further method development.

gLAMP Amplicon Staining Strategies.

Clear MS2 amplicon dot profiles were obtained through post-reaction gel staining with intercalating LAMP dye. Similar profiles were obtained in gLAMP assays for *E. coli* and *Salmonella*. The results highlight the feasibility of adapting established qualitative LAMP assays into quantitative assays via the gLAMP system. However, opening the frame seal chamber and staining the gel after amplification added extra complexity to the assay and may result in amplicon contamination to the surrounding working environment.

To develop a simpler gLAMP without the need for postreaction staining, a primer-dye and primer-quencher duplex (QUASR) was adopted and optimized in this study. In QUASR, the forward internal primer (FIP) is labeled with a fluorophore at the 5' prime end (5' FAM-FIP). The probe is quenched by a complementary primer with a quencher (Iowa Black FQ) at the 3' prime end (qFIP-3' IBFQ). Because the melting temperature (Tm) of the complex is 5-10° C. lower than the reaction temperature (65° C.), the 5' FAM-FIPs are released and behave like regular FIPs during the LAMP reaction. 5' FAM-FIPs are incorporated into the LAMP amplicons when there are target templates present in the sample. After the reaction, extra unincorporated 5' FAM-FIPs are quenched again by the complementary quencher primer qFIP-3' IBFQs. In contrast, 5' FAM-FIPs incorporated into LAMP amplicons would not be quenched because they already form a stable double-strand DNA structure during the LAMP reaction. Compared with nonspecific DNA intercalating dyes (i.e., the LAMP dye), QUASR significantly reduces the issue of false positive results associated with LAMP assays. However, QUASR cannot turn into a quantitative assay in a real-time LAMP scheme because the fluorescent intensity of the reaction mix is constantly at the highest level (all 5' FAM-FIP released) instead of progressively increasing during heat incubation. Therefore, it can only be used as a qualitative assay for end point determination. In preliminary experiments, the study showed that the QUASR primers did not reduce gLAMP amplification efficiency, although a higher concentration of quencher primer (2× of the complementary probe primer) was needed to maintain a clean gel background at the end of the gLAMP reaction. These results suggest that the PEG gel allowed the free movement of the dye-labeled short oligonucleotides, even though the diffusion coefficient would be smaller in the gel matrix than that in a solution. As 5' FAMFIPs were incorporated into the amplicons and accumulated around the initial templates, bright and defined amplicon dots could be directly visualized with a smartphone camera upon blue light exposure. Therefore, QUASR primers were used for further gLAMP optimization.

gLAMP Optimization.

Amplicon dots were visible as early as 20 min under a fluorescence microscope. The dots developed to about 156±33 μm (diameter) after 25 min, and the fluorescence intensity was strong enough to be detected with a smartphone camera. Although the amplicon dots kept increasing in size and reached 212±50 μm after 30 min, the number of dots stayed similar to those at 25 min. Hence, 25 min was chosen as optimal reaction time for MS2 gLAMP. The amplicon dot sizes showed no significant difference at low (1-20 copies per reaction) and medium template (20-200 copies per reaction) concentrations. Under these conditions, amplicon dots were far from each other and had very limited interactions. The dot sizes represented the largest size that the amplicons could develop within the given reaction time, while the size variability in a single gel may result from variable initial template conformation, the degree of template denaturation or from local in homogeneities in the hydrogel structure (due to the free dangling ends, self-looping, or entanglements of macromers). In contrast, the size of amplicon dots at high concentration (200-2000 copies per reaction) were significantly smaller than those formed at the low and medium concentrations. In gLAMP, local competition for enzymes, primers, and dNTP existed, as clear separations were developed among the amplicons close to each other. The smaller amplicon sizes plus the clear boundaries developed at higher template concentration benefited the assay's dynamic range by improving fluorescent dot identifiability. For smartphone camera reading, the optimal assay dynamic range was 1-1000 dots per reaction. When a fluorescence microscope was used for reading results, each gel can accommodate as many as 5000 dots without compromising the precision. Automatic amplicon analysis for microscope and smartphone images was realized by CellProfiler 2.2.0. With appropriate threshold settings, the difference between automatic and manual counting was less than 5%.

For nucleic-acid-based detection methods, a simple DNA and RNA extraction procedure is preferred in point-of-use applications. In gLAMP analysis of MS2-spiked PBS solution, crude samples, samples after a simple heating (95° C., 5 min) pretreatment, and samples extracted with commercial RNA extraction kit showed no significant differences in terms of amplicon dot counts, dot sizes, and the amplicon fluorescence intensity. The current results indicate that the LAMP primers and enzymes (RTx reverse transcriptase and Bst 2.0 DNA polymerase) were able to penetrate the viral capsid at the reaction temperature (65° C.), and denaturing may not be necessary because the viral genome is much smaller compared to that of bacteria.

To evaluate the sensitivity of direct gLAMP, the methods was compared with traditional plaque assays and RT-qPCR. gLAMP amplicon counts showed a good correlation to plaque assay counts ($R^2=0.984$, $p<0.05$). The regression line (slope of 1.036 and intercept of −0.290) indicates that 1 gel amplicon dot was closely equal to 1 PFU. gLAMP achieved a similar lower limit of detection (0.7 plaque-forming units per reaction) compared to that of RT-qPCR (0.4 plaque-forming units per reaction), while RT-qPCR still showed the advantage of a larger upper detection limit. As discussed before, the dynamic range of gLAMP (1-1000 plaque-forming units per reaction) could be increased by reducing the amplicon dot sizes. Accommodating more amplicon dots in a single gel would be desirable for applications such as mutation detection and in-gel sequencing.

Tolerance to Inhibitors.

Enzyme-driven nucleic-acid amplification processes are susceptible to various inhibitory substances (e.g., organic matter and heavy metals) commonly found in environment samples. WW was yellow-brownish and had a chemical oxygen demand (COD) level of 821 mg/L, representing highly contaminated water. LW and PW were clear and contained fewer organic contaminants, with COD levels of 63 and 75 mg/L, respectively. gLAMP assays were successfully carried out in all MS2-spiked environmental water samples (spiking levels of $2\times10^3$ to $2\times10^4$ PFU/mL, equaling 10-100 plaque-forming units per reaction) without RNA extraction. No inhibition was observed because there were no significant differences between the environmental samples and the PBS control in terms of amplicon dot counts ($p>0.05$) as well as dot morphologies. For in-tube real-time LAMP assay, no significant inhibition was found in LW and PW ($p>0.05$). However, 4 out of 6 in-tube real-time LAMP assays were completely inhibited in WW, as no amplification was observed at the end of the reaction (60 min). For RT-qPCR, the assay was completely inhibited in WW because the Cq was beyond the lower limit of detection (Cq max=40). In general, LAMP assays have a more-robust chemistry than PCR in terms of handling complex crude samples because: (1) it employs six primers to initiate the amplification compared with two primers in PCR, (2) the smaller 67 kDa Bst polymerase may enter target cells and viral particles more easily than the 94 kDa Taq DNA polymerase used in PCR, and (3) the yields of LAMP (10-20 micrograms per reaction) are about 50-100 times higher than those of PCR (0.2 micrograms per reaction).

The primary fluorescent DOM peaks for PW and WW were the C-peak and the M-peak, which were associated with humic-like components. The concentration of humic-like DOM in WW was 10-15 times higher than that in LW and PW, which is in agreement with the COD and DOC data. WW also contained low levels of proteinaceous material, as represented by the B-peak and the T-peak. Considering the source of WW, the inhibitors were likely to be organic in origin, similar to those found in urine and feces samples. Urea present in urine samples is known to prevent the noncovalent binding of polymerase enzymes and interferes with primer annealing. The inhibition concentration of urea in PCR was as low as 50 mM, while the tolerance of LAMP to urea was reported to be up to 1.8 M. However, the better performance of the gLAMP in WW cannot be simply attributed to a more-robust LAMP chemistry. It is likely the gel matrix played a more-important role in the enhanced tolerance against inhibitors in WW. First, similar to digital PCR, gLAMP is an end-point amplification-detection assay, counting the final amplification products. Therefore, its quantification is less affected by amplification efficiency. Second, because the DNA and RNA templates were spatially isolated, substrate competition during amplification should be minimized. Moreover depending on their molecular weight, the movement of large molecular-weight organic inhibitors would be restricted by the gel matrix, and thus, the local inhibitor concentrations close to the templates are reduced.

MS2 in Primary Effluent.

MS2 was successfully detected in the RNA extracted from the primary effluent sample by gLAMP (7.8±7.7 PFU/mL). A similar result was obtained in RTqPCR (1.13±0.98 PFU/mL), which confirms the sensitivity and specificity of the gLAMP assay. Culture-based plaque assays generated much higher counts using E. coli C3000 [(6.9±0.4)×$10^3$ PFU/mL] and E. coli Famp [(2.6±0.7)×$10^3$ PFU/mL] as host cells. The discrepancy was because the bacterial hosts used in culture-based plaque assays were susceptible to a wide range of coliphages contained in the sample, while the gLAMP and RT-qPCR assays were specific to MS2.

The foregoing description is illustrative and not restrictive. Although certain exemplary embodiments have been described, other embodiments, combinations and modifications involving the invention will occur readily to those of ordinary skill in the art in view of the foregoing teachings. Therefore, this invention is to be limited only by the following claims, which cover at least some of the disclosed embodiments, as well as all other such embodiments and modifications when viewed in conjunction with the above specification and accompanying drawings.

What is claimed is:

1. A system for detecting a target microorganisms in a sample suspected of containing the target microorganism, comprising:

reaction agents including:

loop mediated isothermal amplification (LAMP) reagents comprising a plurality of primers including a fluorophore labeled primer; and a polyethylene glycol (PEG) hydrogel at a concentration of 10% (w/v) of the reaction agents, the polyethylene glycol hydrogel being formed through Michael addition between a four-arm PEG acrylate having a molecular weight (MW) of 10K and thiol-PEG-thiol having a MW 3.4K, at mole ratio of 1:2, wherein crosslinking of the PEG hydrogel is tuned to form a predetermined mesh size of the PEG hydrogel and a predetermined molecular weight between crosslinkers in the PEG hydrogel that restricts diffusion of DNA/RNA templates of the target microorganism within the PEG hydrogel while allowing free diffusion within the PEG hydrogel of molecules having a MW<100 kDa;

a chamber for combining the reaction agents and the sample to form a mixture;

an incubator configured to heat the mixture;

a slide configured to receive the mixture to allow visual detection of the presence or absence of one or more amplicons that are produced as a result of a LAMP reaction amplifying the DNA/RNA templates of the target microorganism if the target microorganism is present in the mixture, wherein the presence of the amplicons is indicative of the presence of the target microorganism in the sample and the absence of the amplicons is indicative of the absence of the target microorganism in the sample; and a camera configured to visually detect the presence or absence of amplicons in the mixture received on the slide.

2. The system of claim 1, wherein the primers include a primer-dye and primer-quencher duplex.

* * * * *

SEQUENCE LISTING

<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: F3 Forward Primer

<400> SEQUENCE: 1
cttgcgacga tagacttatc                                                    20

<210> SEQ ID NO 2
<211> LENGTH: 18
<212> TYPE: DNA
<213> ORGANISM: Artificial Sequence
<220> FEATURE:
<223> OTHER INFORMATION: B3 Backward Primer

<400> SEQUENCE: 2
tagatgccta tggttccg                                                      18

<210> SEQ ID NO 3
<211> LENGTH: 21
<212> TYPE: DNA
<213> ORGANISM: Artificial Sequence
<220> FEATURE:
<223> OTHER INFORMATION: FIP F1c Primer

<400> SEQUENCE: 3
atcgtatcgt ctcgccatct a                                                  21

<210> SEQ ID NO 4
<211> LENGTH: 22
<212> TYPE: DNA
<213> ORGANISM: Artificial Sequence
<220> FEATURE:
<223> OTHER INFORMATION: FIP F2 Primer

<400> SEQUENCE: 4
ccaccagagc tatattcata tc                                                 22

<210> SEQ ID NO 5
<211> LENGTH: 21
<212> TYPE: DNA
<213> ORGANISM: Artificial Sequence
<220> FEATURE:
<223> OTHER INFORMATION: BIP B1c Primer

<400> SEQUENCE: 5
acaatgggaa atgggttcac a                                                  21

<210> SEQ ID NO 6
<211> LENGTH: 18
<212> TYPE: DNA
<213> ORGANISM: Artificial Sequence
<220> FEATURE:
<223> OTHER INFORMATION: BIP B2 Primer

<400> SEQUENCE: 6
gggtcgcttt gactattg                                                      18

<210> SEQ ID NO 7
<211> LENGTH: 18
<212> TYPE: DNA
<213> ORGANISM: Artificial Sequence -continued

```
<220> FEATURE:
<223> OTHER INFORMATION: LF Primer

<400> SEQUENCE: 7
gattccgtag tgtgagcg                                                   18

<210> SEQ ID NO 8
<211> LENGTH: 22
<212> TYPE: DNA
<213> ORGANISM: Artificial Sequence
<220> FEATURE:
<223> OTHER INFORMATION: LB Primer

<400> SEQUENCE: 8
gctagagtcc atgatattct gg                                              22

<210> SEQ ID NO 9
<211> LENGTH: 21
<212> TYPE: DNA
<213> ORGANISM: Artificial Sequence
<220> FEATURE:
<223> OTHER INFORMATION: 5'FAM-FIP F1c primer

<400> SEQUENCE: 9
atcgtatcgt ctcgccatct a                                               21

<210> SEQ ID NO 10
<211> LENGTH: 22
<212> TYPE: DNA
<213> ORGANISM: Artificial Sequence
<220> FEATURE:
<223> OTHER INFORMATION: 5'FAM-FIP F2 primer

<400> SEQUENCE: 10
ccaccagagc tatattcata tc                                              22

<210> SEQ ID NO 11
<211> LENGTH: 13
<212> TYPE: DNA
<213> ORGANISM: Artificial Sequence
<220> FEATURE:
<223> OTHER INFORMATION: qFIP-3'IBFQ Primer

<400> SEQUENCE: 11
gagacgatac gat                                                        13
```